United States Patent [19]

Dimitri

[11] Patent Number: 6,010,479
[45] Date of Patent: *Jan. 4, 2000

[54] SPECIFIC CATHETER FOR PERCUTANEOUS GASTROSTOMY

[76] Inventor: Mauro Dimitri, 141, Via Delle Gondole, Rome, Italy, 00121

[ * ] Notice: This patent issued on a continued prosecution application filed under 37 CFR 1.53(d), and is subject to the twenty year patent term provisions of 35 U.S.C. 154(a)(2).

[21] Appl. No.: 08/651,948

[22] Filed: May 21, 1996

[30] Foreign Application Priority Data

Sep. 2, 1994 [IT] Italy ................................ RM94A0562

[51] Int. Cl.$^7$ ................................... A61M 29/00
[52] U.S. Cl. ............................. 604/96; 604/525; 606/194
[58] Field of Search ............................. 604/96, 100, 103, 604/264, 524, 525; 606/191, 192, 194

[56] References Cited

U.S. PATENT DOCUMENTS

| | | | |
|---|---|---|---|
| 3,623,484 | 11/1971 | Schulte . | |
| 3,811,448 | 5/1974 | Morton . | |
| 4,642,092 | 2/1987 | Moss | 604/43 |
| 4,976,690 | 12/1990 | Solar et al. | 604/96 |
| 5,102,416 | 4/1992 | Rock | 604/101 |
| 5,195,955 | 3/1993 | Don Michael | 604/101 |
| 5,395,331 | 3/1995 | O'Neill et al. | 604/96 |
| 5,480,392 | 1/1996 | Mous | 604/280 |
| 5,540,679 | 7/1996 | Fram et al. | 606/27 |
| 5,601,539 | 2/1997 | Corso, Jr. | 604/280 |

FOREIGN PATENT DOCUMENTS

| | | |
|---|---|---|
| 182539 | 5/1986 | European Pat. Off. . |
| 533432 | 3/1993 | European Pat. Off. . |
| 25 21011 | 8/1983 | France . |
| 35 32 859 | 3/1986 | Germany . |
| 1262026 | 4/1995 | Italy . |

OTHER PUBLICATIONS

International Search Report for PCT/IT95/00142, Jan. 18, 1996.

*Primary Examiner*—Wynn Wood Coggins
*Assistant Examiner*—A. T. Nguyen
*Attorney, Agent, or Firm*—Finnegan, Henderson, Farabow, Garrett & Dunner, L.L.P.

[57] ABSTRACT

A specific catheter for percutaneous gastrostomy is indicated in all patients undergoing serious abdominal, general, or urologic surgical operations, or during the post-operatory period. This catheter is preferable to the naso-gastric tube which causes discomfort to patients and can be responsible for gastric erosions, gastritis, gastric bleeding, middle ear otitis, pulmonary atelectasis, and pneumonia. Moreover, this catheter is indicated for patients who require a prolonged enteral feeding. The catheter is positioned into the stomach at the end of the surgery through the abdominal wall, lateral to the abdominal incision by a percutaneous technique, and allows the best drainage of acid-mucous secretions from the stomach and duodenum. This catheter because of its material, its tip, its configuration inside the stomach, is a change from the traditional approach to patients improving their quality of life.

10 Claims, 1 Drawing Sheet

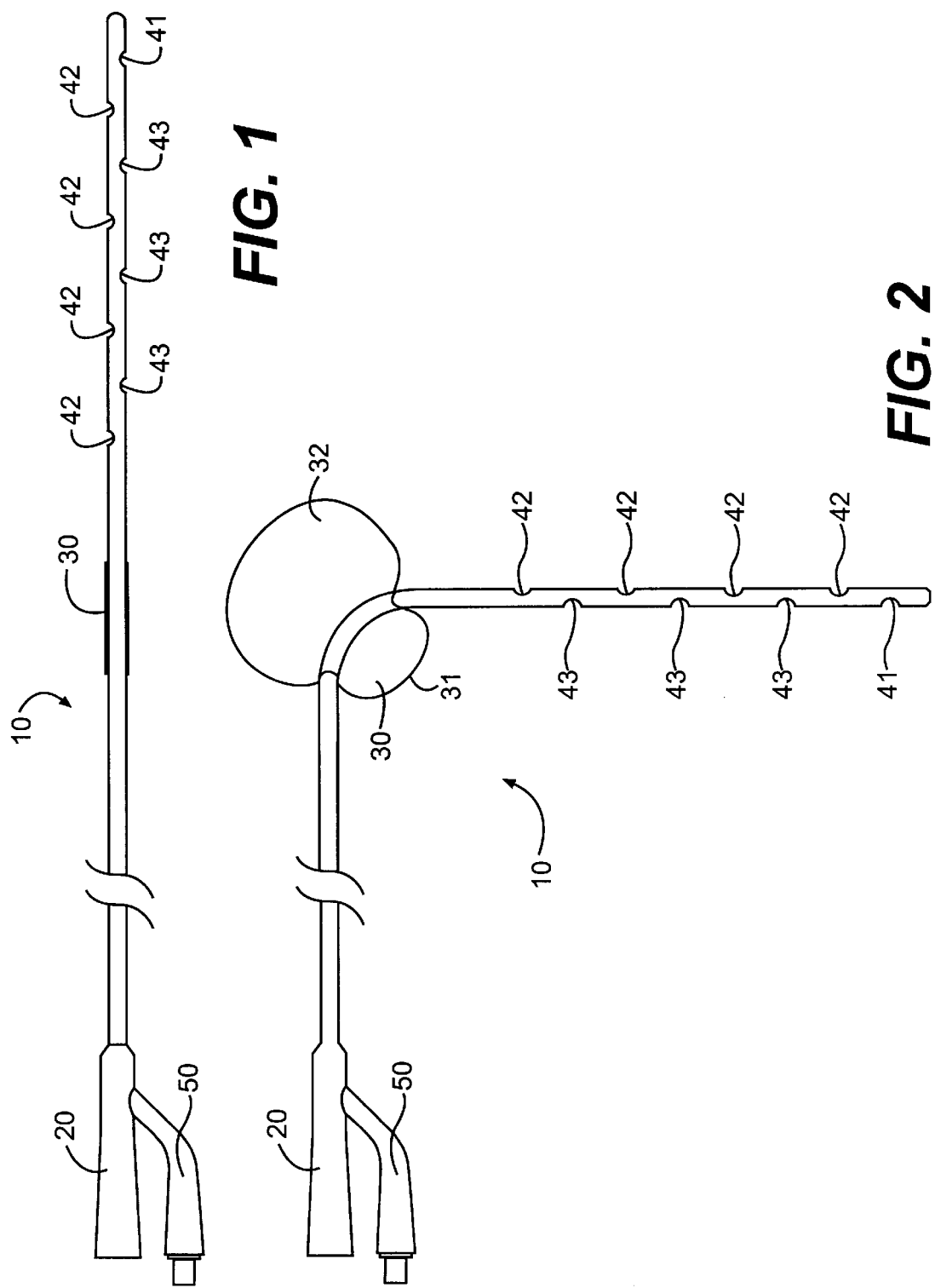

SPECIFIC CATHETER FOR PERCUTANEOUS GASTROSTOMY

BACKGROUND OF THE INVENTION

Patients undergoing serious general and urologic surgical operations very often require a prolonged naso-gastric intubation in the post-operatory period. This intubation is performed by an anesthesiologist at the beginning of surgery by introducing a common naso-gastric tube (catheter). This catheter is useful for draining gastric and duodenal secretions until there are no more effects of general anesthetics on intestinal motility. This approach can cause much discomfort to patients and represents a morbidity factor by causing naso-gastric erosions, gastritis and gastric bleeding, middle ear otitis, pulmonary atelectasis, and pneumonia. The naso-gastric tube obstructs the upper airway, feels like a foreign body in the pharynx, and is not tolerated very well by the majority of patients.

Percutaneous techniques for positioning gastric drainage systems have been described just recently in scientific literature starting in about 1991. The drainage of the stomach and duodenum (gastrostomy) is achieved by introducing a drainage catheter percutaneously through the abdominal wall, lateral to a surgical incision at the end of the surgery. This method presents an alternative to the naso-gastric tube.

Percutaneous gastrostomy is also indicated in those patients who require prolonged enteral feeding not consequent to surgery, and for whom the naso-gastric tube is not adequate. In these particular cases the gastrostomic catheter is introduced percutaneously through the abdominal wall and the gastric wall into the stomach, previously distended with air, under endoscopic guidance (gastroscopy). Smaller bladder (urethral) catheters, for draining urine, are utilized as gastrostomy catheters. Urethral catheters for bladder drainage adapted for gastrostomy have very short tips (from the distal end of the balloon to the apex of the catheter), about 3 cm, having only three holes, and are closed at their apexes. Several materials (latex rubber, polyvinyl, polyurethane, co-polymer, silicone rubber, etc.) are utilized to make catheters of different shapes for many purposes, and are already widely used all over the world, without technical difficulties.

A balloon anchors the catheter and is made of a rubber-elastic material different in size and volume. The balloon can be inflated and deflated through a continent valve, placed tangential and parallel to the funnel of the catheter. The balloon can be fused or fixed to the catheter, depending on the technique.

SUMMARY OF THE INVENTION

The purpose of this invention is to give the patient who requires gastric decompression, the best drainage of gastric and duodenal secretions that a catheter can allow without obstruction, allowing the patient to deambulate early and easily, without the problems of the naso-gastric tube. This is achieved by the particular length of the functional part of the catheter of my invention, the positioning of the balloon, and the unique shape of the balloon itself which determines a particular curvature of the tip of the catheter inside the stomach. Moreover, the catheter is characterized by a wide number of holes along the tip and by the material utilized, silicone rubber, so that the catheter is protected from the acid secretions of the stomach.

Moreover, due to the characteristics of the catheter, it is possible to wash the stomach easily, aspirate the acid and mucous secretions, and administrate foods.

In the catheter of this invention, the balloon assumes a particular shape when inflated due to different thicknesses of the silicone rubber that constitute the wall of the balloon. As a result, the balloon loses its spherical configuration while being inflated and becomes asymmetric and more expanded on one side and less on the opposite side. The balloon's inflation causes the catheter to curve with an angle varying from 45 degrees to 60 degrees, with the more expanded portion of the balloon at the external part of this angle. This curvature of the catheter places its functional part along the longitudinal axis of the stomach with respect to the line of entrance of the catheter which is perpendicular to the abdominal wall.

The catheter of this invention has several holes of adequate diameter and distance to each other in alternate lines along the lateral sides of the catheter. The measure (caliber) of a gastrostomy catheter is important because if it is too big it can after its removal (generally after 8 to 10 days), cause a gastric fistula that discharges into the abdomen or a fistula between stomach and the abdominal wall that discharges to the outside. According to the recent literature, the optimal diameter for a gastrostomy catheter is 14 French. A French is a conventional measurement unit for catheters which follows the equation 1 mm=0.039 inches=3 French.

BRIEF DESCRIPTION OF DRAWINGS

FIG. 1 is an elevational view of the catheter of the invention with a portion of the view broken away. The balloon is shown in a deflated position.

FIG. 2 is an elevational view of the same catheter shown in FIG. 1, but the catheter is angled by the inflation of the balloon so that the tip lies along the longitudinal axis of a stomach.

DESCRIPTION OF THE PREFERRED EMBODIMENT

The technical characteristics of this invention are as follows. The catheter 10 is fused and shaped from silicone rubber. The silicone gives the catheter sufficient rigidity without loosing elasticity. Moreover, the silicone makes the catheter resistant to the acidity of gastric secretions and to mucous incrustations.

The catheter can be classified as a "14 French" catheter. The catheter's total length is 39.5 cm, divided as follows: from the funnel 20 (included) to the base of the balloon 30 the length is 21.5 cm; funnel 20 has a length of 4.5 cm out of the 21.5 cm; the length of the balloon, co-axial to the catheter, is 2 cm if the balloon is fixed to the catheter; or about 1.5 cm if the balloon is fused to the catheter. Both alternatives depend on technical choices in making the catheter. The distal end of the catheter has a length of 16 cm and is measured from the distal end of the balloon to the apex of the catheter.

The apex of the tip of the catheter is cut and opens at a right angle, hole 41.

A number of holes are located along the surface of the tip of the catheter as follows: a total of seven holes are placed in alternate fashion in two lines, each hole measures 5 mm×2 mm; four holes 42 are placed along the side of bigger expansion of the balloon; three holes 43 are placed along the side of smaller expansion of the balloon. The distance between the alternate holes (from one side to the other side) measures 1.27 cm. The first hole of the tip, must start at 3.5 cm of distance from the balloon, along the side of lesser expansion of the balloon.

The balloon 30 has a volume of 10 ml. It expands in an asymmetrical fashion, more on one side, because of differentiate thicknesses of the wall of the balloon that determine a curvature of the tip of the catheter with an angle varying from 45 degrees to 60 degrees so that the tip of the catheter will lie along the longitudinal axis of the stomach. The thicker side 31 and the thinner side 32 are illustrated in FIG. 2.

The catheter has the following dimensions (calibers): The external diameter measures 4.7 mm (corresponding to 14 French) for the whole length of the catheter excluding the funnel portion. Two channels (not shown) run inside the catheter. The first channel has a bigger diameter and measures 2 mm excluding the funnel portion. This channel communicates with the extremities of the catheter, in particular the hole 41 at the apex, the holes 42, 43 along the tip, and with the funnel portion and thus with the outside. The second channel runs within the catheter wall, and measures 0.7 mm; it inflates/deflates the balloon. This extremely thin channel starts at a continent valve 50 implanted for fusion tangential and parallel to the funnel portion of the catheter.

The valve usually measures 6 cm in length, and 1 cm in diameter depending on the type of valve available on the market that is utilized. It needs to be mentioned that during the construction of the catheter the first channel of 2 mm could be slightly improved, reducing the thickness of the catheter wall without losing the proper consistence and rigidity of the catheter.

The funnel has a particular shape in order to be connected to catheter syringes of 60 mL or 100 mL, a current technique of construction.

The catheter material, silicone rubber is mixed with barium sulfate in a proportional quantity that can make the catheter visible, for further evaluations, with conventional X-Ray equipment, confirming its proper position in the stomach.

The funnel of the catheter can be closed with a plug for catheters, at any moment, to evaluate if the intestinal motility has started again, after anaesthesia.

What I claim as my invention is:

1. A catheter for percutaneous gastrostomy, comprising:

a proximal catheter portion;

a distal catheter portion having a wall with holes;

an inflatable balloon located between the proximal and the distal catheter portions, the balloon including a wall having a first side with a first thickness and a second side with a second thickness, wherein the first side of the balloon and the second side of the balloon are disposed on opposite sides of the catheter and the second thickness is greater than the first thickness, the different wall thicknesses causing a greater inflation of the balloon on the first side of the balloon than on the second side of the balloon thereby bending the catheter section and deflecting the distal catheter portion out of alignment with the proximal catheter portion.

2. A catheter for percutaneous gastrostomy, as in claim 1, wherein:

the balloon can inflate to a volume of about 10 mL.

3. A catheter for percutaneous gastrostomy, as in claim 1, further comprising:

four aligned holes located along the distal catheter portion on a side of enlarged expansion of the balloon;

and three aligned holes located along the distal catheter portion opposite of the four holes;

wherein the four holes alternate with the three holes along the distal catheter portion.

4. A catheter for percutaneous gastrostomy, as in claim 3, including:

a first port in the proximal catheter portion in fluid communication with the balloon for inflating the balloon; and a second port in the proximal catheter portion in fluid communication with the distal catheter portion for communicating fluid between the proximal catheter portion and the holes in the wall of the distal catheter portion.

5. A catheter for percutaneous gastrostomy, as in claim 1, further comprising:

a hole at a tip end of the distal catheter portion.

6. A catheter for percutaneous gastrostomy, as in claim 1, wherein:

the catheter is formed of silicon rubber containing barium sulfate for making the catheter visible by using x-rays.

7. A catheter for percutaneous gastrostomy, as in claim 1, further comprising:

a continent valve for maintaining the balloon in an inflated state.

8. A catheter for percutaneous gastrostomy, as in claim 1, wherein:

the distal catheter portion has a length of 16 cm.

9. A method of positioning a catheter for percutaneous gastronomy, comprising the steps of:

introducing a catheter, having an inflatable balloon disposed around a section thereof, into a stomach lateral to an incision in the abdominal wall, the balloon having a wall with a first thickness on one side of the catheter and a second thickness on the other side of the catheter; and inflating the balloon around the section of the catheter such that the balloon expands to a greater size on the first side of the catheter than on the second side of the catheter to cause the catheter section to bend and deflect a distal portion of the catheter into alignment with a longitudinal axis of the stomach.

10. A method of positioning a catheter for operating a catheter for percutaneous gastrostomy as in claim 9, wherein:

the distal portion of the catheter deflects at an angle between 45 and 60 degrees from a proximal catheter portion.

* * * * *